United States Patent [19]

Jahnsen

[11] 3,966,410

[45] June 29, 1976

[54] GROUP EXTRACTION OF ORGANIC COMPOUNDS PRESENT IN LIQUID SAMPLES

[75] Inventor: Vilhelm J. Jahnsen, Lake View Terrace, Calif.

[73] Assignee: California Institute of Technology, Pasadena, Calif.

[22] Filed: June 20, 1974

[21] Appl. No.: 481,065

Related U.S. Application Data

[63] Continuation-in-part of Ser. No. 274,321, July 24, 1972, abandoned.

[52] U.S. Cl. .................... 23/230 B; 23/272 R; 210/31 C; 210/198 C
[51] Int. Cl.² .................. B01D 15/00; B01D 15/08
[58] Field of Search .......... 23/267 RC, 270 R, 271, 23/230 B, 232 C, 272 R; 210/31 C

[56] References Cited

UNITED STATES PATENTS

| | | | |
|---|---|---|---|
| 2,733,135 | 1/1966 | Huckabay | 23/272 R |
| 3,625,652 | 12/1971 | Fujimoto | 23/230 B |
| 3,776,698 | 12/1973 | Eisentraut | 23/230.6 |

OTHER PUBLICATIONS

Partridge, Faraday Soc. Disc No. 7, 1949, pp. 246 to 305.
Treuner, Column Partition Chromatography, 1957, pp. 1 to 15.

Primary Examiner—Stephen J. Emery
Attorney, Agent, or Firm—Lindenberg, Freilich, Wasserman, Rosen & Fernandez

[57] ABSTRACT

An extraction device is disclosed comprising a tube containing a substantially inert, chemically non-reactive packing material with a large surface area to volume ratio. A sample which consists of organic compounds dissolved in a liquid, is introduced into the tube. As the sample passes through the packing material it spreads over the material's large surface area to form a thin liquid film which is held on the packing material in a stationary state. A particular group or family of compounds is extractable from the sample by passing a particular solvent system consisting of a solvent and selected reagents through the packing material. The reagents cause optimum conditions to exist for the compounds of the particular family to pass through the phase boundary between the sample liquid and the solvent of the solvent system. Thus, the compounds of the particular family are separated from the sample liquid and become dissolved in the solvent of the solvent system. The particular family of compounds dissolved in the solvent, representing an extract, exits the tube together with the solvent through the tube's nozzle, while the rest of the sample remains on the packing material in a stationary state. Subsequently, a different solvent system may be passed through the packing material to extract another family of compounds from the remaining sample on the packing material.

10 Claims, 4 Drawing Figures

GROUP EXTRACTION OF ORGANIC COMPOUNDS PRESENT IN LIQUID SAMPLES

ORIGIN OF INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

CROSS REFERENCE TO RELATED APPLICATION

This application is a continuation-in-Part of application Ser. No. 274,321, filed July 24, 1972, now abandoned.

BACKGROUND OF THE INVENTION

1. Field of the Invention

The present invention is generally directed to the extraction of chemical compounds from a sample and, more particularly, to a method of separating families of organic compounds present in a liquid sample.

2. Description of the Prior Art

Samples consisting of a liquid, in which chemical compounds, such as organic compounds, are dissolved are often processed to extract different groups of compounds which are present in the sample. One process is often referred to as liquid-liquid extraction. In this process the extraction is achieved by the addition of a suitable extracting solvent (or solvents) which is generally immiscible in the liquid of the original sample and by causing the desired compounds to become separated from the sample liquid and become dissolved in the extracting solvent. Extraction is caused by one of two phenomena: (a) Physical solution; and (b) chemical reaction and solution.

In the former, extraction takes place because the desired compounds are initially more soluble in the extracting solvent than in the liquid of the original sample hereinafter referred to as the sample liquid. In other words, the partition coefficients of the compounds are in favor of the extracting solvent. Thus, when the latter is introduced into the sample the desired compounds become dissolved in it. In the extraction based on chemical reaction and solution, a reagent (or reagents) is introduced with the extracting solvent, which upon contact with the compounds of interest forms derivatives which are more soluble in the extracting solvent than in the sample liquid.

These techniques and phenomena are well known by those familiar with the art. For example, in the field of toxicology, blood or urine samples which are aqeuous liquids are processed by means of extracting organic solvents, to determine the presence of groups or individual drugs (organic compounds) in the samples. With the ever increasing number of samples being processed, the prior art liquid-liquid extraction techniques, through relatively simple, have been found to be too time-consuming, requiring the use of different devices and containers, and the attention of experienced technicians, all of which add to the sample processing cost.

Typically, present state of the art liquid-liquid extraction consists primarily of introducing the sample, e.g., blood into a phase separator or vessel to which an appropriate solvent with reagents are added. Generally, the volume of solvent is much larger than the sample volume. The phase separator is then shaken for a period of time. The sample, due to the turbulent action upon it and the fact that its liquid is immiscible with the solvent, tends to break up into droplets, which travel through the larger volume of the solvent. This action produces surface to surface contact between the sample liquid droplets and the solvent. As a result of this contact the desired compounds, whose partition coefficients were adjusted by the reagents to favor the solvent, become separated from the sample liquid and become dissolved in the solvent. Thus, a mass transfer of the desired compounds takes place from the original sample liquid to the solvent. Clearly, the greater the contact area between the sample liquid and the solvent, the faster and more efficient is the extraction. This is achieved by insuring a sufficiently long shaking period.

Thereafter, the solvent, now containing the desired compounds, is separated from the rest of the sample by passing the phase separator content through a filter. The separated compounds which are dissolved in the solvent are often referred to as the extract or solutes. If an emulsion is created as a result of the shaking, centrifugation is required to remove the emulsion. If more than one extract from a single sample is desired, i.e., if more than one group or family of the compounds in the sample are to be extracted therefrom, after removing the first extract, the procedure must be repeated. This is done by adding new solvents with other reagents, suitable for the extraction of the second extract, to the remaining sample in a second phase separator or to a new quantity of the same sample. Thereafter, the shaking, filtering and centrifugation are repeated.

This procedure, which is well known by those familiar with the art, is quite lengthy and requires nearly continuous operator performance and attention, and therefore it is quite costly. Furthermore, it requires a considerable amount of equipment such as a centrifuge, drying apparatus and elements, such as the filters, which are discarded after each filtration step.

In another technique for extracting an extract from an aqueous liquid sample, i.e., a sample consisting of an aqueous liquid in which compounds are dissolved, e.g., deproteinized blood or urine, a column containing a non-ionic resin is used. The resin attracts only non-ionic compounds which pass through it. In use the aqueous liquid sample pH is first adjusted and, thereafter, it is passed through the column. The non-ionic resin attracts the non-ionic compounds of the sample and the rest of the sample, which is not attracted, passes out of the column. To remove any residue the column is washed and only thereafter is the extract, comprising the attracted non-ionic compounds, eluted by passing a solvent through the column. Thus, this technique also requires a substantial number of steps. To extract a second extract from the liquid sample its pH must be adjusted to a different value and the above steps must be repeated in the same or another column.

Since the number of extractions which are performed in various laboratories, such as those engaged in clinical chemistry or in forensic studies is very large, a need exists for a new device for and method of extracting extracts from samples which do not require the above procedures to be followed. Basically, a need exists for a new method to simplify the extraction of families of chemical compounds, hereinafter referred to as extracts or solutes, from liquid samples.

OBJECTS AND SUMMARY OF THE INVENTION

It is a primary object of the present invention to provide a new method for the extraction of extracts from a liquid sample.

Another object of the invention is to provide a new method for extracting extracts from a liquid sample, without requiring the performance of phase separation, as performed in the prior art.

These and other objects of the invention are achieved by providing a device comprising an elongated tube with opposite open ends. In one embodiment the tube is in the shape of a hollow cylinder with reduced diameter at one end to form an output nozzle. The other end of the tube, opposite the nozzle, is open and serves as the inlet end. Supported in the tube between the inlet end and the nozzle is an inert chemically non-reactive packing material which has a large surface area to volume ratio. In use the tube is positioned vertically with the inlet end at the top. A liquid sample, hereinafter simply referred to as the sample, is introduced into the tube through the tube's inlet end. As the sample reaches the packing material it tends to spread as a thin liquid film on the material's large surface area and is held thereon in a stationary state. The only function of the packing material is to provide a large surface area over which the sample spreads out as a thin liquid film without reacting with the packing material, or becoming decomposed thereby. The entire sample remains on the packing material as the thin liquid film as long as no other matter is introduced into the tube.

To extract an extract, i.e., a particular family of compounds from the thinly spread out sample, a solvent system is introduced into the tube. As used herein, the term solvent system refers to a solution of a solvent (or solvents) which is immiscible in the original sample liquid and one or more reagents selected on the basis of the desired extract. As the solvent system passes through the packing material it comes in contact with the thinly spread out sample over the very large surface area over which the sample is spread out. Thus, intimate contact between the sample and the solvent system is achieved. The reagents are chosen to cause the partition coefficients of only the desired compounds to be extracted to change in favor of the solvent. Thus, as the solvent system comes in contact with the spread out sample the desired compounds become dissolved in the solvent and exit therewith, as the desired extract, through the tube's nozzle. The rest of the compounds in the sample remain dissolved in the sample liquid and remain in the stationary state on the packing material.

After extracting one extract, a subsequent extract consisting of a different family of compounds, may be extracted from the remaining sample by merely passing a second solvent system through the tube. This second solvent system causes the partition coefficients of the compounds to be included in the second extract to move in favor of the solvent in the second solvent system and be extracted out of the tube with the extracting solvent.

The novel features of the invention are set forth with particularity in the appended claims. The invention will best be understood from the following description when read in conjunction with the accompanying drawings.

DESCRRIPTION OF THE PREFERRED EMBODIMENTS

Figure 1A:
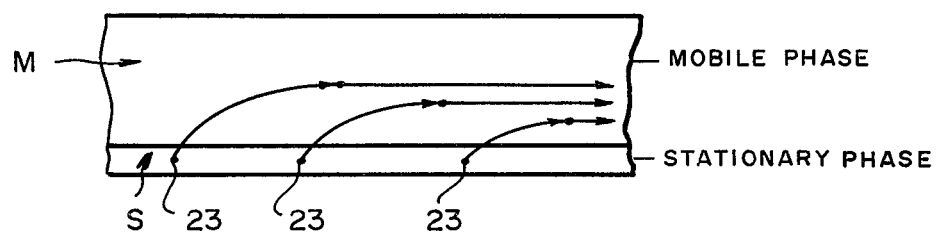
FIGS. 1a and 1b are diagrams useful in explaining the difference between the present invention and the field of chromatography.
Figure 1B:
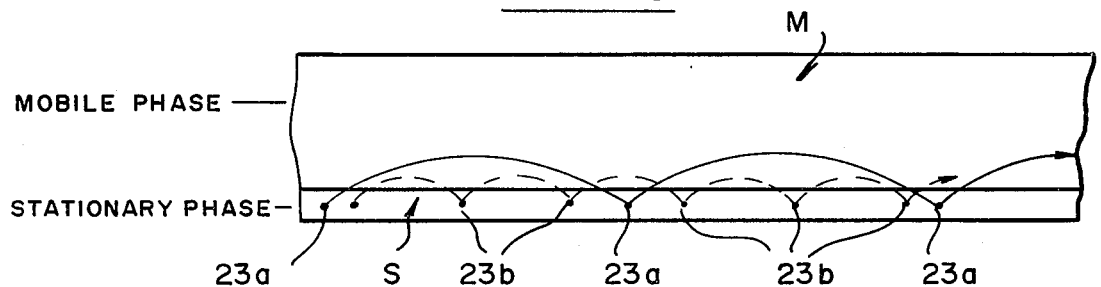
Figure 1:
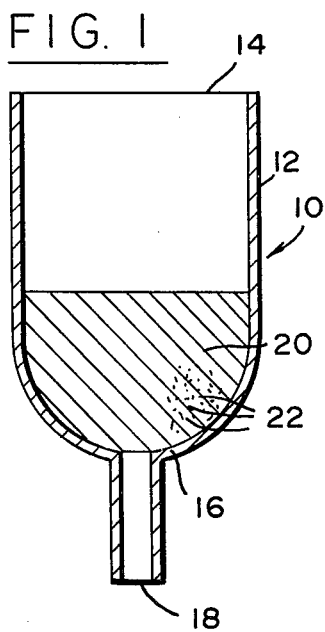
FIG. 1 is a cross-sectional view of one embodiment of the present invention.

Attention is first directed to FIG. 1 wherein one embodiment of the extraction tube, used in the practice of the present invention, is designated by numeral 10. The tube consists of a hollow cylinder 12 which extends from an open inlet end 14 to an opposite end 16. The latter is funnel-shaped, terminating in an open nozzle 18. When the tube is disposed vertically, as shown in FIG. 1, in the absence of any packing material in the tube, any liquid, introduced through inlet end 14, would flow out and exit through nozzle 18.

In accordance with the present invention an inert chemically non-reactive packing material 20 fills a portion of the cylinder 12 near end 16. Various examples of such a packing material will be described hereinafter. The packing material 20 is one with a large surface area to volume ratio. When a liquid sample, such as blood or urine, is introduced into the tube through inlet end 14 it flows toward the nozzle 18 by gravity. As it encounters material 20 it tends to spread out as a thin liquid film on the material's large surface area. Thus, instead of exiting the tube through nozzle 18 it is retained on the large surface area of the material 20 in a stationary state. As a result, the compounds, dissolved in the sample liquid, are spread out over a large surface area.

The amount of packing material is chosen to insure that practically the entire sample is retained by the material 20, with the latter becoming practically saturated by the sample. As previously stated, the packing material is one which is inert and which for all practical purposes, does not react chemically with the sample. Its only function is to provide a larger surface area over which the sample spreads out as a thin liquid film, with the chemical cmpounds dissolved in it, and to retain the sample in a stationary state, for subsequent treatment. In FIG. 1, dots 22 designated the sample on the material 20.

To extract any particular family of compounds, herein referred to as an extract or solute, from the sample, a particular solvent system is introduced into the tube through inlet end 14. The solvent system is a mixture of reagents and a solvent which is immiscible in the sample liquid. The reagents are chosen so that as the solvent system passes through the material 20 the reagents cause the compounds of the desired extract to move through the phase boundary between the sample liquid and the solvent. Alternately stated, the reagents are chosen to change the partition coefficient of the compounds to be extracted from the sample liquid in favor of the solvent. Consequently, the desired compounds or the extract separate from the sample liquid and become dissolved in the solvent. Since the packing material is practically saturated by the sample practically none of the solvent is retained by the packing material and therefore the solvent flows through the material 20 and exits the tube through nozzle 18. Since the extract is dissolved in the solvent it too exits the tube through the nozzle together with the solvent. Any appropriate container may be positioned below the nozzle 18 to receive the solvent with the desired extract dissolved therein.

It should be stressed that since the liquid sample is spread out as a thin film on the large surface area of the packing material 20 as the solvent system passes therethrough it comes in contact with the sample over a very large surface area, yet in relatively small volume. This provides optimum liquid-liquid interface between the sample, and the solvent system. Alternately stated, the solvent system's interface with the compounds is direct and over a large surface area, thereby facilitating the transfer of the desired extract from the sample to the solvent without manual or automatic shaking. Such shaking is required in prior art liquid-liquid extraction.

Compounds can be extracted from an aqueous liquid sample with reagents which adjust pH value of the sample so that certain compounds become deionized while the reamining ionized compounds remain in the aqueous solution. In the present invention the reagents of each solvent system are chosen to adjust the pH value of the sample to a particular value in order to deionize only compounds in a particular family which are to be included in the extract. The rest of the sample's compounds remain ionized in the sample and therefore in a stationary state on material 20. They do not exit the tube.

The reagents may be introduced into the tube together with the solvent as part of the solvent system. Alternately, the reagents may be added to the sample before the latter is introduced into the tube. In such a case, the solvent system need only include the solvent in which the extract is to be dissolved as the solvent passes through the adjusted sample which is spread out on the large surface area of material 20.

It should be stressed that in the present invention the reagents adjust the sample so that the partition coefficients of all those compounds in the sample which are to be extracted as a group or family are heavily in favor of the solvent. Thus, extraction as herein taught, is on a family or group basis. There is no attempt at discrete individual extraction of individual compounds within any family. The compounds, which are extracted due to the partition coefficient heavily favoring the solvent, once they become dissolved in the solvent remain dissolved therein and do not return into the sample liquid, as they pass through the rest of the packing material toward the nozzle 18.

This point may be highlighted by referring to FIG. 1a wherein the area labeled S is assumed to represent a stationary phase such as the sample with the compounds represented by circles 23 on the packing material 20 and area M represents a moving phase such as the solvent flowing through the packing material. In the present invention once the compounds move from the stationary phase S to the moving phase M, i.e., become separated from the sample liquid and become dissolved in the solvent, they remain dissolved therein. They do not return back to the sample liquid, represented by the stationary phase. Thus, the novel process of the invention is one in which a unidirectional (from the stationary to the moving phase) transfer takes place of all the compounds in the sample which belong to the family to be extracted. As previously explained, the transfer is achieved by adjusting the pH of the sample so that only the partition coefficients of only those compounds which are to be extracted is heavily in favor of the solvent.

It should further be stressed that the present invention eliminates the need for shaking a vessel, e.g., a phase separator containing an adjusted sample and a solvent. Such shaking is required by prior art liquid-liquid extraction techniques. As previously pointed out such shaking is required to insure proper contact between the sample and the solvent. In the present invention the optimum contact is achieved by spreading the sample over the large surface area, yet small volume of the packing material. Thus, when the solvent is introduced, as it passes through the packing material, it automatically contacts the sample over the large surface area over which the sample is spread out without the need for shaking.

Various presently known packing materials are suitable such as packing material 20. These include cellulose fiber materials, such as absorbent cotton, filter paper and multilayered pressed alpha-cellulose sheets and glass fiber materials, such as glass wool or pyrex wool. Also, materials of ceramic fibers, such as the material sold by Carborundum Corporation under the trademark Fiberfrax or tissue paper, containing a mixture of cellulose and glass fibers, may be used. Irrespective of which material is actually used as the packing material 20, it should be of high purity so as not to contaminate the sample, and possess a high degree of absorbency in order to absorb and thereby retain the sample therein in the stationary state. Furthermore, it should have a high ratio of surface area to volume, so as to enable the sample to spread out as a thin film over the packing material surface, and enable the solvent to pass therethrough. Alternately, the packing material should have an open fibrous matrix with high void to fill ratio to allow optimum solvent flow therethrough and interfacial contact with the sample.

Tests, yielding very satisfactory results, were performed with packing material 20 consisting of multilayered alpha-cellulose sheets which were purified, dried and then cut into wafers ¼ inch to ⅛ inch in diameter with a uniform packing density of about 0.150 g/cc. Also, packing materials consisting of rolled thin sheets of ceramic wool or rolled filter paper were used with great success. However, as should be appreciated any known packing material, exhibiting the above described properties, may be used.

It is appreciated that the choice of solvents is dictated by the nature of the sample liquid and the compounds to be extracted and by the degree of purity desired. To extract organic compounds from aqueous samples, solvents which are immiscible in an aqueous liquid are used. Among the general purpose solvents for such use are chloroform, methylene, chloride, ethyl acetate, benzene and ether. Hexane and iso-octane are useful non-polar solvents. Quite often a mixture of several solvents may be used as the extracting solvent. Previously pointed out reagents are used to adjust the sample pH and thereby facilitate the separate extraction of different families of compounds.

The teachings of the present invention though not limited to is particularly applicable to extracting families or organic compounds often referred to as drugs from samples such as biological samples, including blood and urine.

As is appreciated, all organic compounds belong to one of the following four classes:
1. Acids strong : sulfonic, carboxylic...
weak : phenolic 2. Bases
   strong : quarternary ammonium...
   weak : secondary amine...

3. Amphoterics
   Having both acid and basic functions : Amino acids, alkaloids...

4. Neutrals
   Having neither acid nor basic functions : Hydrocarbons, esters, ethers...

Except for the neutrals, organic compounds are greatly affected by the pH of the aqueous (water) solutions in which they are situated.

A. At acid pH's (0–7) due to the relative abundance of hydrogen ions in the milieu, organic acids are satisfied, and therefore they are nonionized and less polar. Consequently their solubility in water is greatly reduced. Their partition coefficient is in favor of an organic solvent, such as chloroform, with which they may come in contact. When this contact occurs, they cross the interfacial boundary between the aqueous solution and the solvent and dissolve in the latter, e.g., chloroform.

Bases and the basic functions of amphoterics do ionize in the acid milieu. Thus, they become more polar and hydrated. Their partition coefficient is in favor of the aqueous solution and therefore they are not extracted by an organic solvent such as chloroform, when coming in contact therewith. Neutrals remain unaffected by pH. They retain their integrity and individual polarity. The more polar, the greater the partition coefficient is in favor of water as opposed to chloroform. The less polar, the readier they dissolve in chloroform and thus are extracted.

B. At basic pH's (7–14), the relative paucity of the hydrogen ions causes organic acids to ionize, become more polar and hydrated and thus less soluble in organic solvents.

Bases however, become satisfied, less polar, thus less soluble in water and more soluble in organic solvents such as chloroform.

The acid functions of the amphoteric becomes more polar due to ionization and behaves as an organic acid.

C. At optimum pH's, amphoterics achieve a perfect balance between their acid and basic functions which are then both satisfied and the compound becomes neutral, less polar thus more soluble in chloroform. This optimum pH is 8.5 for morphine.

It is thus seen that pH has a profound effect upon the extractability of organic compounds by an organic solvent. It is the effect of the sample pH on the extractability of organic compounds from the sample that is utilized in practicing the present invention. Indeed this effect enables the successive extraction of several families of compounds from the sample, once the latter is spread out on the packing material. For example, by first adjusting the sample pH to about 4 (less than 8.5) and thereafter passing therethrough an organic solvent, all the acidic and neutral drugs, present in the sample, will be extracted as a family. However, any amphoteric and basic compounds in the sample will remain in its liquid, which remains on the packing material 20. Then, the remaining sample pH may be adjusted to about 8.5. The amphoteric compounds will be extracted by passing another quantity of solvent through the tube. Thereafter, the pH of the remaining sample may be adjusted to about 12 to extract any basic compounds in the sample.

Figure 2:
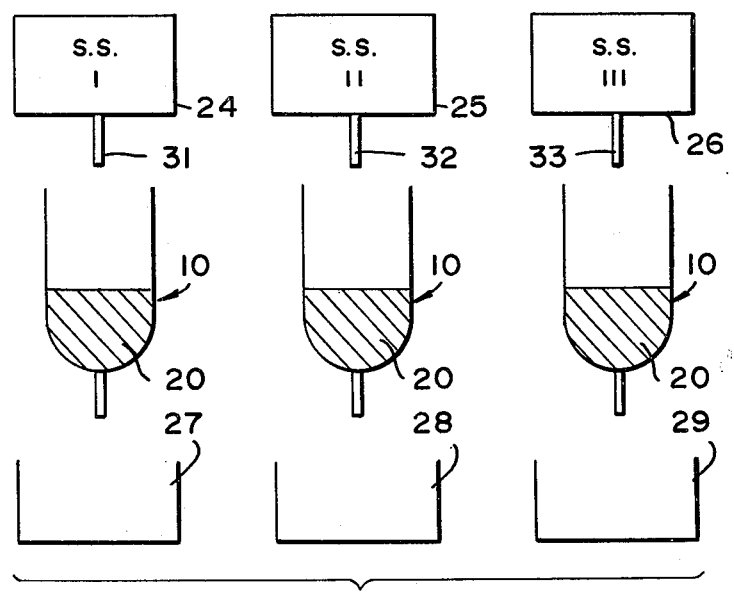
FIG. 2 is a diagram useful in explaining the successive extractions in accordance with the present invention.

Such a process is diagrammed in FIG. 2, wherein blocks 24–26 represent sources of solvent systems (SS) I–III. SSI is assumed to include an organic solvent with reagents which when passing through the sample in tube 10 adjusts the pH to about 4 (less than 8.5). The acidic and neutral drugs dissolve in the solvent and exit therewith through nozzle 18 into container 27. Thus, the latter includes all the acidic and neutral compounds previously present in the sample. The remaining sample remains in tube 10. The reagents assumed to be included in SSI may be passed through the sample prior to the injection of the solvent or simultaneously therewith.

SSII is assumed to include a solvent and reagents which when passing through the sample which remained in tube 10 adjust its pH to about 8.5. Thus, as the solvent of SSII passes through the tube, either together with the reagents or after their introduction, all the amphoteric compounds in the remaining sample are extracted in container 28. SSIII is assumed to include a solvent and reagents which when passing through the remaining sample adjust its pH to about 12. Thus, the basic drugs are extracted and are collected, together with the extracting solvent in container 29.

It should be stressed that each extraction is a family or group extraction. That is, all the compounds present in the sample which belong to the particular family are extracted together and exit the tube together in the extracting solvent. Except for the extracted compounds the rest of the sample remains in a stationary state on the packing material 20 as a thin liquid film. The family which is to be extracted clearly depends on the pH value to which the sample is adjusted either before or together with the introduction of the extracting solvent. For example, if the pH is adjusted to less than 7, the family to be extracted is only that including the acidic and neutral compounds. On the other hand, if the sample is first adjusted to a pH of 8.5 the family may include both the amphoteric and the neutral drugs. Clearly, if the sample is initially adjusted to a pH value of 12, the extracted family would include all the basic and neutral drugs present in the original sample.

It is apparent that each of the solvent systems SSI–III may include a mixture of more than one solvent and reagents if the pH adjustment is to be performed during extraction. If the sample pH is adjusted before the extracting solvent is introduced, each solvent system may consist of only one or more extracting solvents.

As previously pointed out, to extract the acidic compounds the pH value should be adjusted to about 3–5 (less than 8.5). If the pH is adjusted prior to extraction any of the all purpose organic solvents may be used in SSI. If the pH is adjusted during extraction SSI may consist of solvent mixtures such as ethyl acetate : methylene chloride : methanol : glacial acetic acid, 50:45:4:1, by volume, or methylene chloride : glacial acetic acid, 99:1, or chloroform : glacial acetic acid, 99:1, or ethyl acetate : glacial acetic acid, 99:1, may be used with excellent results. However, it should be clear that other mixtures of solvents and reagents may be used as long as the sample pH is adjusted during extraction to about 3–5 and an appropriate organic solvent (or solvents) pass through the spread-out sample to extract the desired acid and neutral compounds, which are present in the sample.

The extraction of amphoteric compounds, such as morphine alkaloids from an aqueous sample, such as urine, may be successfully achieved in accordance with the present invention by first adjusting the pH of the urine in tube 10 to about 8.3 with sodium bicarbonate and thereafter introducing SSII consisting of a mixture of ethyl acetate-methylene chloride-methanol-concentrated ammonium hydroxide, 50:45:4.9:0.1 by volume. Such a solvent system raises the sample pH to 8.5 as it passes the sample and facilitates the extraction of the amphoteric compounds. If the urine (sample) pH was previously adjusted to 8.5, the SSII may consist of a mixture of methylene chloride-methanol 90:10 by volume. Such a mixture was found to be particularly useful for the extraction of morphine alkaloids.

To extract the basic compounds, the solvent system SSIII should include reagents which would adjust the sample (e.g., urine) pH to about 11 or 12. If the urine is adjusted prior to extraction, SSIII can consist of any of several of solvents such as chloroform, ether or ethyl acetate. If the pH is to be adjusted during extraction SSIII could include reagents so that as SSIII passes through the sample its pH is adjusted to about 11 or 12. A mixture of ethyl acetate : methylene chloride : methanol : concentrated : ammonium hydroxyde, 50:45:3:2 was found to be extremely efficient in extracting the basic organic compounds.

It should be stressed that in accordance with the present invention after each extract is extracted the rest of the sample remains on the packing material in a stationary state. That is, all the nonextracted compounds remain dissolved in the sample liquid on the packing material. They remain thereon until a subsequent solvent is introduced and the remaining sample has its pH adjusted to a different value and thereby cause a different family of the remaining compounds to be extracted. All the compounds in the sample which belong to the family being extracted move en mass, unidirectionally, from the sample liquid to the solvent in which they dissolve, and which carries them out of the tube. Once dissolved in the extracting solvent the compounds do not return back and forth between the sample liquid and the extracting solvent, as previously explained in connection with FIG. 1a.

This extraction process is unlike the process taking place in liquid-liquid chromatography, which is one form of chromatography. All forms of chromatography may be defined as controlled migration, where sample components are selectively retained by a stationary phase. The stationary phase is either an active solid or a liquid. The mobile phase is either a liquid or a gas. In the chromatographic process there is a constant and repeated partitioning of the compounds between the stationary phase and the mobile phase in order to achieve individual separations of the compounds from other individual compounds.

Liquid-liquid chromatography is the closest form of chromatography with which the present invention may be erroneously analogized. In liquid-liquid chromatography the sample such as an aqueous solution, e.g., water is held on the packing material of the column and is regarded as the stationary phase. The mobile or moving phase is typically an immiscible or partially immiscible solvent or mixture of solvents. As the mobile phase migrates through the column the compounds of the sample, which are to be separated, distribute themselves between the two phases according to their respective partition coefficients in these two phases. Since there are discrete differences between these partition coefficients, the compounds of the sample migrate at different rates through the column and thereby are separated since they exit the column at different times.

This basic chromatographic process may best be summarized in connection with FIG. 1b wherein areas S and M respectively represent the stationary and moving phases. The solid arrows represent the interphase travel of one compound 23a and the dashed arrows represent the interphase travel of a different compound 23b. Product 23a is assumed to have a partition coefficient which is more in favor of the mobile phase than that of product 23b. Each of these compounds moves back and forth between the two phases. However, product 23a returns less often to the stationary phase than compound 23b. Thus, the former exits the column before product 23b.

By comparing FIGS. 1a and 1b it should be apparent that the process of the present invention differs from that of liquid-liquid chromatography. In the process of the present invention the sample's pH is adjusted to a value either before the extracting solvent is introduced or together with it, so that any compound in the family to be extracted has its partition coefficient highly in favor of the solvent. Therefore, the compound separates from the sample and moves unidirectionally into the solvent. Once it becomes dissolved in the solvent it does not return back into the sample liquid. Also, with the process of the present invention family or group extraction is performed. That is, all the compounds whose partition coefficients were adjusted to be heavily in favor of the solvent dissolve in the extracting solvent and exit together as a family. They do not exit the tube at different times, which is the basis of identifying compounds by the chromatographic process.

The present invention also differs from other liquid type chromatographic processes. For example in liquid-solid chromatography, which is basically an adsorptive process, the packing material adsorbs the sample and exerts a definite and selective action upon the various compounds of the sample. When a solvent is introduced, representing the moving phase, migration of compounds takes place because of constant repeated adsorption and desorption of the components between the two phases. In ion exchange chromatography there is an exchange of ions between the sample and the packing material, which represents the stationary phase. Separation is achieved due to different affinities of ions of different compounds for the packing material.

Summarizing the foregoing description in accordance with the present invention, a tube is provided which contains a packing material which is inert and which does not react chemically with a liquid sample which passes through the tube. The packing material has a large surface area to volume ratio so that the sample spreads out as a thin liquid film on the surface of the packing material. The sample remains spread out over the packing material surface in a stationary state. It does not decay while being on the packing material, nor does it separate from the packing material unless subsequent steps are performed. As used herein, the term sample or liquid sample refers to a liquid, which contains compounds to be extracted. Urine or blood containing organic compounds, such as drugs, or drug traces are but two examples of such samples. The sample liquid refers to the liquid portion of the sample in which the compounds are dissolved.

After the sample is spread out on the packing material, the pH of the sample is adjusted to a desired value so that all the compounds present in the sample and belonging to a given family, e.g., acidic, amphoteric, basic, etc., have their partition coefficients heavily in favor of a solvent which is made to pass through the packing material either together with or after the introduction of the reagents. As a result, all the compounds which are present in the sample and which belong to the particular family to be extracted, become dissolved in the solvent and exit the tube therewith as the desired extract. The compounds of sample which were not extracted remain in a stationary state in the sample liquid on the packing material. A second extract of a different family of compounds may be extracted by adjusting the pH of the remaining sample to a different value and thereafter passing a solvent through the pH adjusted sample.

Both the chemistry involved herein, as well as the terminology used are not new. That is, liquid samples consisting of a liquid in which chemical compounds are contained, the solute or extract comprising a selected family of compounds, solvents immiscible in the liquid of the sample which removes selected families of compounds and reagents which adjust the pH of the sample to change the partition coefficient in a direction to enable the extract to become soluable in the solvent, are all well known, for example in the fields of toxicology and endocrinology, and to those skilled in these arts. By way of illustration, and not by way of limitation, liquid samples may be blood, urine, bile, stomach content or homogenized tissue, liquid or liquidified foods and beverages, waste water or water for human and animal consumption, industrial preparations...etc.. The chemical compounds contained in such liquid samples may be drugs and drug metabolities, normal dietary metabolities, normal or abnormal body metabolities, hormones, lipids, vitamins, poisons and contaminants useful and deleterious compounds...etc.. Reagents may be ammonia or acetic acid. Immiscible solvents may be chloroform, ethyl acetate ether, butyl chloride, etc..

All of the foregoing and much more are set forth in publications such as "A Manual of Analytical Toxicology", by Irving Sunshine, PHD, editor, and published by Chemical Rubber Co. of Cleveland, Ohio, copyright 1971. Another publication is "Methods of Analysis for Alcholoids, Opiates, Marijuana, Barbituates and Dangerous Drugs", published by the Bureau of Narcotics and Dangerous Drugs, U.S. Department of Justice, Publication No. 341 (Rev. 6–67). Another publication is "Survey of Analytical Methods for Determination of Drugs and Body Fluids", published by the Bureau of Narcotics and Dangerous Drugs, U.S. Department of Justice, No. SCID-1R-8 (1972). And finally, still another publication is one by Clark, E. G. C., entitled, "Isolation and Identification of Drugs", Pharmaceutical Press, London, 1969.

The method and means described herein and recited in the claims, for bringing a known solvent, in contact with a known liquid sample, for extracting therefrom a known particular extract, more quickly then thought possible heretofore, using inexpensive apparatus, is novel. All of the chemicals used in practicing the method and means are, for example, those described in the cited publications and no experimentation is required in view of the vast amount of information on the subject provided in the literature, of which the foregoing is just a sample.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A method of extracting from a liquid sample, consisting of an aqueous liquid in which chemical compounds are contained, an extract, comprising a selected family of said compounds, the steps comprising
   providng a substantially hollow tube with inlet and outlet openings and a packing zone therebetween,
   placing a dry, substantially inert, chemically non-reactive packing material which has a large surface area to volume ratio within said packing zone,
   directing through said open inlet to said packing material said liquid sample, whereby as it comes in contact with said packing material it spreads out as a thin liquid film over the large surface area of said packing material and is held thereon in a stationary state, and
   rapidly removing said extract directly from said packing material in bulk out of said outlet opening, without selective fractional migration within the packing zone substantially immediately after the time required for an organic solvent, which is immiscible with the liquid of said sample, to pass through said packing material which is holding said sample as a thin liquid film spread over its large surface area,
   said step of rapidly removing said extract comprising passing a reagent through said packing material to adjust the pH of said extract in said liquid sample to provide said extract with a partition coefficient value biased very heavily in favor of a solvent, which is immiscible with the liquid of said sample, relative to said sample,
   passing said solvent, which is immiscible with the liquid of said sample through said packing material, in bulk through said packing material whereby it will exit said outlet opening carrying said extract therewith.

2. The method as described in claim 1 wherein said reagent is first passed through to adjust the sample pH to a selected value, and thereafter the solvent is passed through said pH-adjusted sample.

3. The method as described in claim 1 wherein the reagents and said solvent are simultaneously passed through said sample.

4. The method as described in claim 1 further including the steps of passing through said packing material after said one family of chemical compounds is extracted, other reagents and at least one solvent which is also immiscible in the liquid of said sample,
   said subsequently passed through reagents adjusting the pH of the sample remaining on said packing material to a value different from said first value so that the partition coefficient of all the chemical compounds in the remaining sample, belonging to a second family different from the family previously extracted, become heavily in favor of said at least one solvent when compared to the coefficient value in favor of said liquid of said sample and become dissolved in said solvent, said solvent exiting said tube through said outlet and with the extract comprising all the compounds previously present in said sample and belonging to said second family, said sample, except for the removed extracts, remaining as a thin liquid film on said packing material.

5. The method as described in claim 4 wherein said sample is a biological sample, the liquid thereof is an aqueous liquid, said compounds are organic compounds, said solvent is an organic solvent, and said reagents first adjust the pH to a value in the range between 3 and 5 for extracting the first family of organic compounds comprising the acidic and neutral compounds, and thereafter adjust the pH in the range of 8:5 to extract the second family which includes amphoteric compounds, and thereafter adjust the pH in the range of 12 to extract a third family which includes basic compounds.

6. A method of directly extracting from the liquid sample, consisting of an aqueous liquid in which organic chemical compounds are contained, an extract, comprising a selected family of said compounds, the steps comsisting of providing a substantially hollow tube with inlet and outlet openings and a packing zone therebetween, placing in said packing zone a dry, substantially inert, non-reactive fibrous packing material having a large surface area to volume ratio, applying said liquid sample to said fibrous packing material to spread said liquid sample as a thin liquid film over the large surface area of said fibrous packing material, to be held thereon in a stationary state, and removing an extract from said packing zone directly, in bulk, and without selective fractional migration within said packing zone, substantially immediately after the interval required for a solvent immiscible in the liquid in said sample, to traverse through said packing material over which said thin liquid film is held, comprising passing through said packing material selected reagents and in bulk at least one organic solvent which is immiscible in the aqueous liquid of said sample, said reagent adjusting the pH of said sample to a value at which the part ion coefficients of all of the organic compounds of said sample, belonging to said selected family, become heavily biased in favor of said organic solvent, relative to said aqueous liquid, whereby said selected family of compounds becomes dissolved in said organic solvent and pass out of said packing zone therewith.

7. The method as described in claim 6 wherein said reagents adjust the pH of said sample to a range of 3:5, whereby said extract definable as a first extract includes the acidic and neutral organic compounds in said sample.

8. The method as described in claim 7 further including the steps of passing through said packing material after said extract is extracted reagents and at least one solvent which is also immiscible in the liquid of said sample, said subsequently passed through reagents adjusting the pH of the sample remaining on said packing material to a value different from said first value, so that the partition coefficients of all of the components of the compounds in the remaining sample belonging to a second family different from the family previously extracted, become heavily in favor of said solvent relative to the partition coefficient in fabor of said aqueous liquid to become dissolved therein, said solvent exiting said tube through said outlet with the extract comprising all the compounds previously present in said sample and belonging to said second family, said sample, except for the extracted compounds, remaining as a thin liquid film on said packing material.

9. A method of extracting from a liquid sample consisting of an aqueous in which chemical compounds are contained, an extract, comprising a selected family of said compounds, the steps of comprising establishing a packing zone in a substantially hollow tube having an input opening and an output opening on opposite ends thereof, packing said packing zone with a dry, chemically inert, packing material having a large surface area to volume ratio, applying all of said liquid sample to through said input opening to said packing material to physically hold said liquid sample spread as a thin liquid film in a stationary phase over the large surface area of said material, and removing said extract directly from all of said packing material, in bulk, out of said output opening and without selective fractional migration within said packing zone, substantially immediately after the time required for a solvent, which is immiscible with the liquid of said sample, to traverse said packing material over which said liquid film is held, said step of removing said extract from said packing material comprising passing in bulk through said packing material a solvent system including an organic solvent which is immiscible in the liquid of said sample, and a reagent for adjusting the pH of said extract to a value at which the partition coefficient of said extract is so heavily biased in favor of said immiscible solvent that it moves out of solution in said liquid sample and into solution with said solvent, whereby said solvent system passes through and out of said packing zone substantially immediately after traversing the packing material holding said liquid film, removing said extract therewith leaving the remainder of said sample spread as a thin liquid film over the surface area of said packing material.

10. A method of successively extracting from a sample, comprising an aqueous liquid containing different families of chemical compounds, different extracts, each extract including a selected family of said compounds, the steps consisting of providing a substantially hollow tube having an upper inlet end and an opposite outlet end and a packing zone therebetween which is packed with a dry inert chemically non-reactive packing material having a large surface area to volume ratio, pouring said sample into said tube through said inlet and onto said packing material, whereby said sample spreads over the large surface area of said packing material is physically held thereon in a stationary state, successively removing different extracts in bulk, directly from said packing material and out of the outlet end of said tube, without selective fractional migration within the packing zone, substantially immediately after the interval required for a solvent for a particular extract which is immiscible with the liquid of the sample, to travel through the region of said packing material over which said thin liquid film is held, comprising successively passing through said packing material, for each extract to be removed, a selected reagent and in bulk an organic solvent which is immiscible in the aqueous liquid of said sample, said selected reagent adjusting the pH of each extract to a value so that the partition coefficient of all of the compounds within a family which is to be removed, are biased heavily in favor of said immiscible solvent relative to the bias to said aqueous liquid and become dissolved in said organic solvent, whereby each successively added organic solvent, together with the extract dissolved therein passes through said packing zone and out of said inlet end of said tube in bulk, leaving the remainder of said liquid sample dispersed as a thin liquid film on said packing material.

* * * * *